(12) United States Patent
Gliner et al.

(10) Patent No.: US 9,091,603 B2
(45) Date of Patent: Jul. 28, 2015

(54) TEMPERATURE SIMULATOR FOR THERMOCOUPLE-BASED RF ABLATION SYSTEM

(71) Applicants: Vadim Gliner, Haifa (IL); Assaf Govari, Haifa (IL)

(72) Inventors: Vadim Gliner, Haifa (IL); Assaf Govari, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 310 days.

(21) Appl. No.: 13/626,951

(22) Filed: Sep. 26, 2012

(65) Prior Publication Data

US 2014/0086273 A1    Mar. 27, 2014

(51) Int. Cl.
 G01K 15/00    (2006.01)
 A61B 18/04    (2006.01)
 A61B 18/14    (2006.01)
 A61B 17/00    (2006.01)

(52) U.S. Cl.
 CPC .......... G01K 15/007 (2013.01); A61B 18/1492 (2013.01); A61B 2017/00725 (2013.01)

(58) Field of Classification Search
 CPC ............................................ A61B 2018/00577
 USPC ......................................................... 374/1–5
 See application file for complete search history.

(56) References Cited

U.S. PATENT DOCUMENTS

| 4,850,356 | A | * | 7/1989 | Heath ............................ 607/142 |
| 5,743,903 | A | * | 4/1998 | Stern et al. ...................... 606/31 |
| 6,038,488 | A | * | 3/2000 | Barnes et al. .................. 700/161 |
| 6,226,542 | B1 | | 5/2001 | Reisfeld |
| 6,301,496 | B1 | | 10/2001 | Reisfeld |
| 6,814,733 | B2 | | 11/2004 | Schwartz et al. |
| 6,892,091 | B1 | | 5/2005 | Ben-Haim et al. |
| 6,997,924 | B2 | | 2/2006 | Schwartz et al. |
| 7,156,816 | B2 | | 1/2007 | Schwartz et al. |
| 7,536,218 | B2 | | 5/2009 | Govari et al. |
| 7,869,854 | B2 | * | 1/2011 | Shachar et al. ............... 600/374 |
| 2002/0038092 | A1 | * | 3/2002 | Stanaland et al. ............. 600/509 |
| 2006/0150134 | A1 | * | 7/2006 | Shinomiya ....................... 716/11 |
| 2009/0030411 | A1 | | 1/2009 | Werneth et al. |
| 2009/0306641 | A1 | * | 12/2009 | Govari et al. .................... 606/33 |
| 2011/0066147 | A1 | * | 3/2011 | He et al. .......................... 606/33 |
| 2011/0218526 | A1 | * | 9/2011 | Mathur ............................. 606/33 |

FOREIGN PATENT DOCUMENTS

WO   WO 2012/071388 A2   5/2012

* cited by examiner

*Primary Examiner* — Lisa Caputo
*Assistant Examiner* — Nasir U Ahmed
(74) *Attorney, Agent, or Firm* — Wayne C. Jaeschke, Jr.

(57) ABSTRACT

Testing a thermocouple-based RF ablation system is carried out by connecting a temperature simulator to an ablator module. The ablator module is operative to vary a radiofrequency power output thereof in a predefined manner in response to predefined variations in a temperature signal from the simulator. The method is further carried out by delivering RF power from the ablator module to the temperature simulator, and while delivering RF power, performing the steps of: communicating temperature signals from the temperature simulator to the ablator module, varying the communicated temperature signals, and verifying that a variation in the power output of the ablator module in response to varying the temperature signals conforms to the predefined manner.

17 Claims, 3 Drawing Sheets

TEMPERATURE SIMULATOR FOR THERMOCOUPLE-BASED RF ABLATION SYSTEM

BACKGROUND OF THE INVENTION

1. Field of the Invention

This invention relates to tissue ablation systems. More particularly, this invention relates to simulated operation of an RF generator in tissue ablation system.

2. Description of the Related Art

Cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. By selectively ablating cardiac tissue by application of energy via a catheter, it is sometimes possible to cease or modify the propagation of unwanted electrical signals from one portion of the heart to another. The ablation process destroys the unwanted electrical pathways by formation of non-conducting lesions.

U.S. Patent Application Publication No. 2009/0030411 by Werneth et al. describes an ablation catheter in which a thermocouple can be used to measure the temperature local to the thermocouple prior to, during or after the delivery of ablation energy. It is explained that when an ablation is performed, maintaining the tissue at a temperature below a threshold is required. Information recorded from the thermocouple is used to adjust energy delivery or to modify its frequency, based on temperature information analysis.

U.S. Patent Application Publication No. 2011/0218526 provides another example of a thermocouple in an ablation system, which electrodes may be electrically coupled to an output portion of an RF generator, and each thermocouple may be electrically coupled to a feedback portion of the RF generator. A processor accepts an input voltage and produces an output voltage, based on feedback signals from the thermocouples, and then adjusts a duty cycle modulator as well as an amplitude modulator according to the feedback signals.

SUMMARY OF THE INVENTION

There is provided according to embodiments of the invention an apparatus for testing a tissue ablation system, which includes emulation circuitry connectable to an ablator module being tested, the ablator module has an adjustable radiofrequency (RF) power output and a monitor display. The emulation circuitry includes a first arm of a first thermocouple metallic material linked to the power output of the ablator module, and a second arm of a second thermocouple metallic material connected to the monitor display. A return pathway extending from the first arm to the ablator module permits passage of RF current and blocks direct current (DC). An adjustable voltage source producing a DC potential is connected via an output circuit across the first arm and the second arm, the output circuit having a greater resistance to RF current than to direct current.

According to an aspect of the apparatus, the return pathway includes a DC blocking capacitor.

According to a further aspect of the apparatus, the output circuit includes a chain of resistors connected in series with an inductor.

According to one aspect of the apparatus, the inductor includes a plurality of ferrite inductors in connected in series with the adjustable voltage source.

According to yet another aspect of the apparatus, a value of the inductor is 1 mH.

There is further provided according to embodiments of the invention a method of testing a thermocouple-based RF ablation system, which is carried out by connecting a temperature simulator to an ablator module. The ablator module is operative to vary a radiofrequency (RF) power output thereof in a predefined manner in response to predefined variations in a temperature signal. The method is further carried out by delivering RF power from the ablator module to the temperature simulator, and while delivering RF power, performing the steps of: communicating temperature signals from the temperature simulator to the ablator module, varying the communicated temperature signals, and verifying that a variation in the power output of the ablator module in response to varying the temperature signals conforms to the predefined manner.

There is further provided according to embodiments of the invention a method of testing a thermocouple-based RF ablation system, which is carried out by connecting a temperature simulator to an ablator module. The ablator module is operative to vary a radiofrequency (RF) power output thereof in a predefined manner in response to predefined variations in a temperature signal and has a temperature display monitor. The method is further carried out by delivering RF power from the ablator module to the temperature simulator, while delivering RF power, performing the steps of: communicating temperature signals from the temperature simulator to the ablator module, varying a potential of the communicated temperature signals in accordance with known temperature-dependent potentials of a thermocouple junction to represent respective temperatures, and calibrating the temperature display monitor to conform to the respective temperatures represented by of the communicated temperature signals.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

Aspects of the present invention may be embodied in software programming code, which is typically maintained in permanent storage, such as a computer readable medium. In a client/server environment, such software programming code may be stored on a client or a server. The software programming code may be embodied on any of a variety of known non-transitory media for use with a data processing system, such as a diskette, hard drive, electronic media or CD-ROM. The code may be distributed on such media, or may be distributed to users from the memory or storage of one computer system over a network of some type to storage devices on other computer systems for use by users of such other systems.

The term "couple" or "coupled" is intended to mean either an indirect or direct connection. Thus, if a first device is coupled to a second device, that connection may be through a direct connection, or through an indirect connection via other devices and connections, or via inductive or capacitive coupling.

Figure 1:
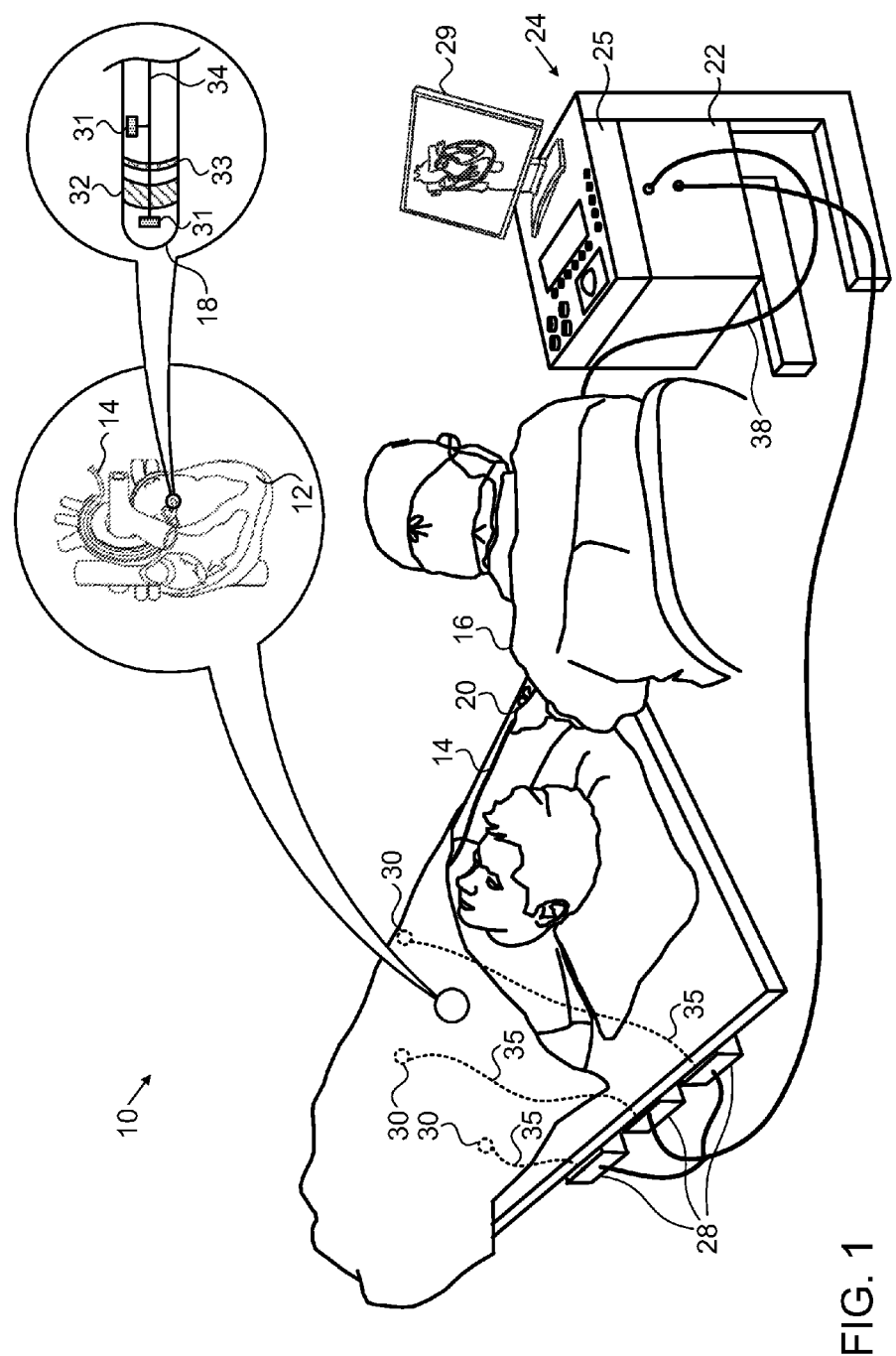
FIG. 1 is a pictorial illustration of a system for performing diagnostic and therapeutic procedures on a heart of a living subject, which is constructed and operative in accordance with a disclosed embodiment of the invention.

Turning now to the drawings, reference is initially made to FIG. 1, which is a pictorial illustration of a system 10 for performing diagnostic and therapeutic procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall at an ablation target site. Optionally, electrical activation maps may then be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a positioning processor 22, located in a console 24.

Ablation energy and electrical signals can be conveyed to and from the heart 12 through one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24, are disposed between the ablation electrodes 32 and have connections to the cable 34.

Wire connections 35 link the console 24 with body surface electrodes 30 and other components of a positioning subsystem. The electrodes 32 and the body surface electrodes 30 may be used to measure tissue impedance at the ablation site as taught in U.S. Pat. No. 7,536,218, issued to Govari et al., which is herein incorporated by reference. A temperature sensor such as thermocouples 31, may be mounted on or near the ablation electrode 32 and optionally or near the sensing electrode 33. The thermocouples 31 are connected to the electrode circuit as described in further detail below.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

The positioning processor 22 is an element of a positioning subsystem in the system 10 that measures location and orientation coordinates of the catheter 14.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem may employ impedance measurement, as taught, for example in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14 and to analyze the electrical signals from the electrodes.

Typically, the system 10 includes other elements, which are not shown in the figures for the sake of simplicity. For example, the system 10 may include an electrocardiogram (ECG) monitor, coupled to receive signals from one or more body surface electrodes, to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided.

In order to accurately ablate tissue, for example according to known procedures in which tissue temperature is an important variable, it is desirable to understand and model the behavior of the ablation catheter in actual operation. This can be done, according to embodiments of the invention, using a jig, which behaves as a temperature simulator, and which is connected to an RF generator. The simulator operates while the RF generator is active by separating a relatively high power RF current from a low power DC current, using a capacitor to provide a preferred low-impedance path for the RF component. The DC component is a voltage of about 40 μV, approximating typical thermocouple junction voltages, and which is detected and quantitated. By externally controlling a DC source for the voltage, the detected voltage and therefore the simulated temperature is immediately affected, irrespective of the activity of the RF generator.

Embodiments of the present invention separate the two effects, i.e., the junction potential, $V_j$, and the RF power, P, in a simulation/calibration jig. Positive and negative terminals of the jig are connected to the μV input of the generator and to ground, respectively.

Figure 2:
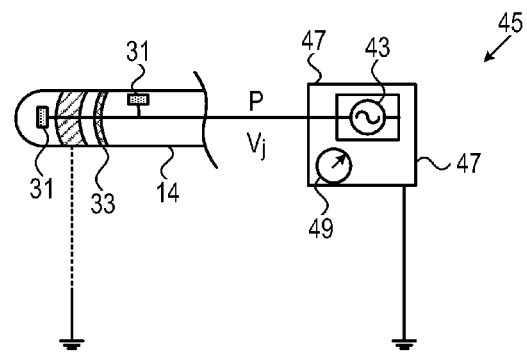
FIG. 2 is a schematic diagram of a thermocouple-based RF ablation system, in accordance with an embodiment of the invention.

Reference is now made to FIG. 2, which is a schematic diagram of a thermocouple-based RF ablation system 45, in accordance with an embodiment of the invention. A tissue ablation module, which is realized as an RF generator module 47 includes an RF generator 43 and a display 49, which presents a microvolt DC reading.

The generator module 47 is connectable to catheter 14 in actual ablation operation. The generator 43 is adjustable, and the direct current (DC) response of thermocouples 31 occurs during actual operation of the catheter 14. The DC output of the thermocouples 31 ($v_j$) can thus be correlated with the power (P) produced by the RF generator 43 and measured using the display 49. However, in this system, the accuracy of the monitored DC output and hence the temperature reading is affected by the presence of induced RF current in the thermocouple circuit.

Figure 3:
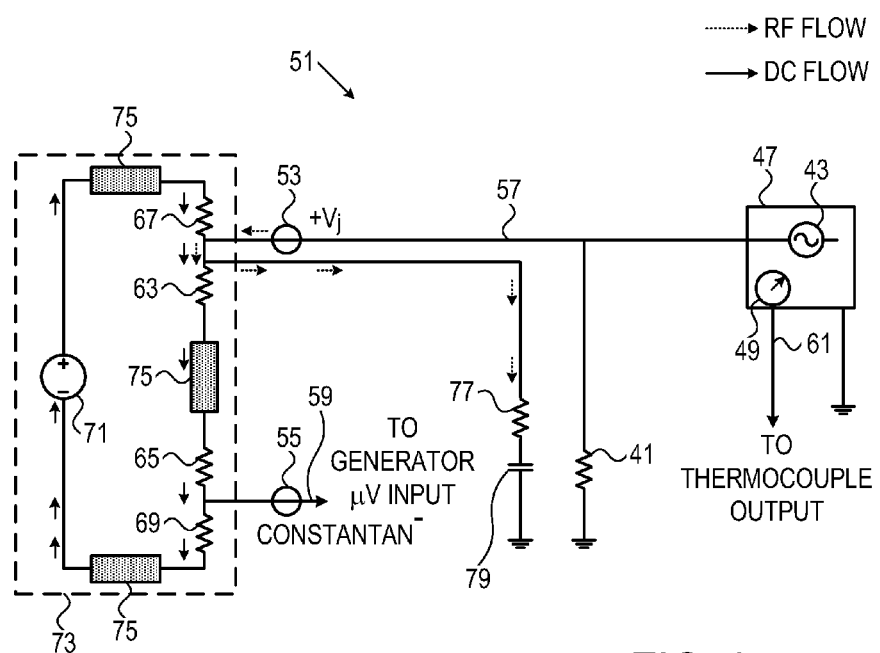
FIG. 3 is a detailed electrical schematic of a temperature simulator, which simulates operation of the ablation system shown in FIG. 2, in accordance with an embodiment of the invention.

Reference is now made to FIG. 3, which is a detailed electrical schematic of a jig 51, which simulates operation of the ablation system 45 (FIG. 2), in accordance with an embodiment of the invention. In the circuitry shown in FIG. 3, the flows of direct current and RF current are indicated by solid arrows and arrows drawn as broken lines, respectively.

As noted above, in actual operation of an ablation system, the RF power produced by the generator module 47 heats resistive tissue of a patient, causing ablation of part of the tissue. In the jig 51 the resistive tissue is represented by a load resistor 41, which is connected to the RF power output of a generator 43. The resistor 41 needs to be able to dissipate power on the order of 25 W.

A positive terminal 53 made of copper-constantan and a constantan wire 55 are thermocouple metallic elements of the sort that may implement a thermocouple in an ablation catheter. In such a catheter, the thermocouple may be in physical contact with the ablation electrode or more loosely coupled to the ablation electrode without actual physical contact. In the jig 51, RF current is present at the positive terminal 53. In the example of FIG. 3, the positive terminal 53 uses a copper conductor 57 (carrying the power) as one "arm" of the thermocouple—the other arm being the constantan wire 55. The potential $V_j$ generated at the positive terminal 53, arising from the junction temperature, is typically of the order of microvolts. The potential may be fed back to the power generator via negative terminal 59, which typically uses the measured potential to control the power delivered by the generator. Other thermocouple metallic elements and alloys may be substituted for copper and constantan in the positive terminal 53 and negative terminal 59.

A generator suitable for use as the generator 43 is the nMARQ™ RF generator produced by Biosense Webster. This generator has a microvolt input 61 and the capability of displaying the power delivered by the electrode and the impedance "seen" by its output terminal. The generator also displays the temperature of the electrode, using the junction potential $V_j$ described above that is received via the microvolt input 61 and shown on the display 49. This temperature is generally not the actual temperature of the patient tissue or of the electrode-tissue interface. As stated in the manual "The temperature displayed on the nMARQ Multi-Channel RF Generator does not represent the temperature of the tissue nor the temperature of the interface between the electrode and the tissue." The temperature registered by the thermocouple (and displayed by the nMARQ generator), and the temperature of the tissue are different because of the heating effect of the RF power.

As shown in the schematic, known value resistors 63, 65 are placed across the copper-constantan junction of the thermocouple. The resistors 63, 65 are part of a resistor chain that includes resistors 67, 69. The resistors 63, 65, 67, 69 have values of 150-200 Ohms. The chain is connected to a variable DC source 71, which combines with the DC voltage $V_j$ and appears across positive terminal 53 and negative terminal 59. The Model NIPCI-6073 data acquisition tool, available from National Instruments Corporation, 11500 N. Mopac Expwy, Austin, Tex. 78759-3504, is suitable for the source 71. RF current in a portion of the circuitry delineated by a box 73 is largely eliminated by the presence of 1 mH ferrite inductors 75, and also by connecting a resistor 77 in series with a 0.15 mF DC blocking capacitor 79 to provide a return path having low impedance to RF, and leading from the positive terminal 53 to ground. As a result, DC is blocked from the return path, but RF is permitted. At the same time, RF current is effectively blocked from a second circuit, which is a path formed by source 71, inductors 75 and the resistor chain, and which has a greater resistance to RF current than to DC current. This is largely due to the reactance of the inductors 75 seen by the RF source. However, the combined DC output of the source 71 and the voltage $V_j$ flows readily in the second circuit, and DC voltage appears at the negative terminal 59 and at the microvolt input 61 of the generator module 47.

The effect is to separate the DC potential between the positive terminal 53 and the negative terminal 59 from the RF current produced by the generator module 47. The separation of the DC potential and the RF power allows the jig to be used for two purposes:

(1) Simulating different values of the thermocouple potential $V_j$ and the RF power P independently of each other by adjusting the outputs source 71 and the generator 43. This type of simulation allows various ablation algorithms built into generators (such as the nMARQ RF generator) to be modified or evaluated. Such algorithms typically use values of the potential $V_j$ to control the RF power P. The jig 51 allows simulations of scenarios, such as rapid temperature excursions, e.g., beyond safety limits, or very stable temperatures. When such scenarios occur, the response of the generator module 47 can be evaluated.

(2) Calibration of the value of the potential $V_j$ for different values of the power P and other variables such as change of the power P with time. The electromotive force produced by copper-nickel alloys such as constantan as a function of temperature is well-known. In a calibration mode, any desired temperature can be simulated, and the readout of the generator module 47 may be adjusted to correct errors. This calibration can be elaborated to correct for errors that vary according to the levels of RF power being produced. Such calibrations are typically performed at the factory, but may be repeated by maintenance personnel, or even by an operator if desired.

While the generator 43 and the display 49 may be integral, as in FIG. 3, this is not essential, and they may be provided separately. The simulations and calibrations described above may be performed in any case.

The following procedures are explained for convenience with respect to the circuitry shown in FIG. 3, but they are not limited to the particular configuration shown therein.

Figure 4:
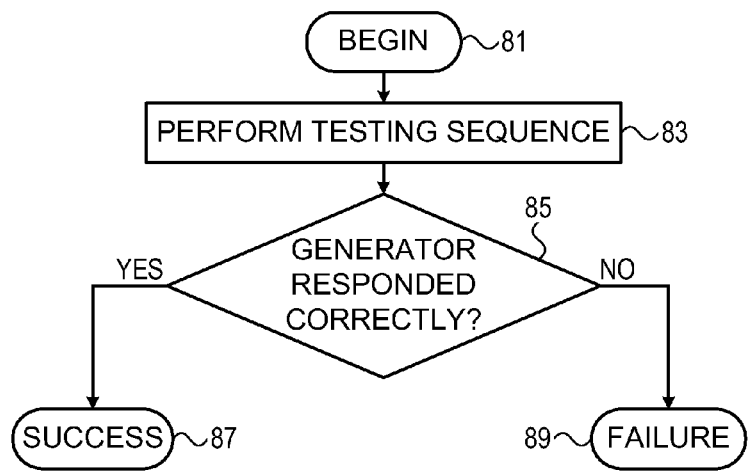
FIG. 4 is a flow chart of a method of operating a temperature simulator for thermocouple-based RF ablation system, in accordance with an embodiment of the invention.

Reference is now made to FIG. 4, which is a flow chart of a method of operating a temperature simulator for thermocouple-based RF ablation system, in accordance with an embodiment of the invention. At initial step 81 the jig 51 is connected to the generator module 47, to the display 49 and the direct current source 71.

Next, at step 83, the power output of the generator module 47 and the source 71 are independently adjusted so as to simulate a sequence of events, which the generator module 47 is expected to recognize and to respond in accordance with its internal programming.

For example, the simulator may be adjusted such that the display 49 initially registers 38° C. and progresses to 44° C. while the power varies up to 25 W.

In an alternative testing sequence, the simulator may be adjusted such that the display 49 initially registers 38° C. and progresses to an upper temperature limit of 47° C., with oscillations of +/−2° C., during which the power may reach a target of 25 W and then drop, so as to maintain the temperature readings below 47° C.

In yet another alternative testing sequence, designed for testing safety of the ablator, the display 49 may initially be set to register 47° C. and progress to 80° C. It is expected that the generator module 47 will issue an alert indicating an abnormally high temperature and will produce control signals intended to reduce or discontinue power output in order to stop the ablation.

Next, at decision step 85, it is determined if the generator module 47 has responded to the testing sequence as programmed. If the determination is affirmative, then control proceeds to final step 87 where a successful result is reported.

If the determination at decision step 85 is negative, then control proceeds to final step 89 where failure is reported.

Figure 5:
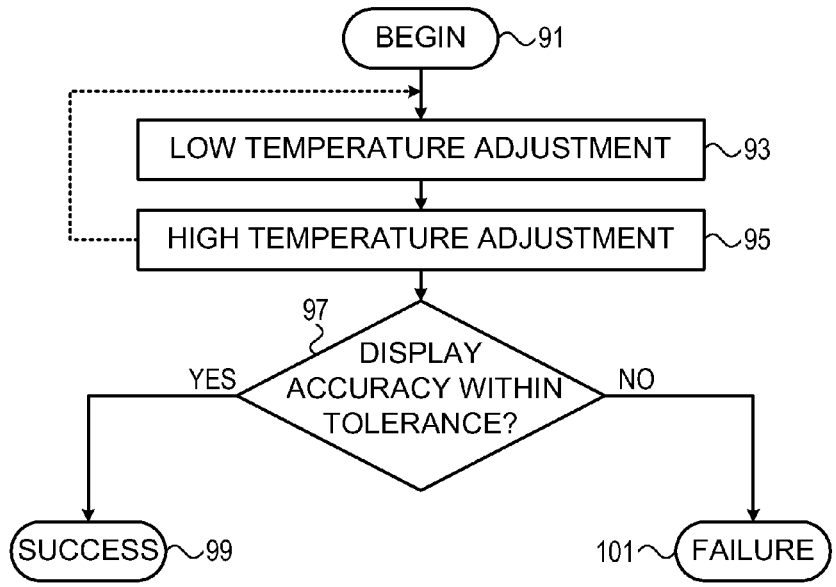
FIG. 5 is a flow chart of a method of operating a temperature simulator for thermocouple-based RF ablation system to calibrate an RF generator, in accordance with an embodiment of the invention.

Reference is now made to FIG. 5, which is a flow chart of a method of operating a temperature simulator for thermocouple-based RF ablation system to calibrate an RF generator having a microvolt input, in accordance with an embodiment of the invention.

At initial step 91, the jig 51 is connected to the generator module 47, to the display 49 and the direct current source 71.

Next, at step 93, the source 71 is adjusted to simulate a first temperature, e.g., 25° C. A bias control in the generator module 47 is adjusted such that the display 49 reads 25° C. The generator module 47 may be activated to produce power at an operational level to assure that the display 49 continues to read 25° C.

Next at step 95, the source 71 is adjusted to simulate a second temperature, e.g., 75° C. A sensitivity control in the generator module 47 is adjusted such that the display 49 reads 48° C. The generator module 47 may be activated to produce power at an operational level to assure that the display 49 continues to read 75° C.

Steps 93, 95 may be iterated, varying the bias and sensitivity controls as necessary to improve the quality of the readings of the display 49.

Next, at decision step 97, it is determined if the readings of the display 49 are accurate within a defined tolerance limit. If the determination is affirmative, then control proceeds to final step 99 where a successful result is reported.

If the determination at decision step 97 is negative, then control proceeds to final step 101 where failure is reported.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

What is claimed is:

1. An apparatus for testing a tissue ablation system, comprising:
emulation circuitry connectable to an ablator module being tested, the ablator module having an adjustable radiofrequency (RF) power output and a monitor display, the emulation circuitry comprising:
a first arm comprising a first thermocouple metallic material linked to the power output of the ablator module;
a second arm comprising a second thermocouple metallic material connected to the monitor display;
a return pathway extending from the first arm to the ablator module, the return pathway permitting passage of RF current and blocking direct current (DC);
an adjustable voltage source producing a DC potential and connected via an output circuit across the first arm and the second arm, the output circuit having a greater resistance to RF current than to direct current.

2. The apparatus according to claim 1, wherein the return pathway comprises a DC blocking capacitor.

3. The apparatus according to claim 1, wherein the output circuit comprises a chain of resistors connected in series with an inductor.

4. The apparatus according to claim 3, wherein the inductor comprises a plurality of ferrite inductors in connected in series with the adjustable voltage source.

5. The apparatus according to claim 3, wherein a value of the inductor is 1 mH.

6. A method of testing a thermocouple-based RF ablation system, comprising the steps of:
connecting a temperature simulator to an ablator module, the ablator module operative to vary a radiofrequency (RF) power output thereof in a predefined manner in response to predefined variations in a temperature signal;
delivering RF power from the ablator module to the temperature simulator;
while performing the step of delivering RF power, performing the steps of:
communicating temperature signals from the temperature simulator to the ablator module;
varying the communicated temperature signals; and
verifying that a variation in the power output of the ablator module in response to varying the communicated temperature signals conforms to the predefined manner.

7. The method according to claim 6, wherein the temperature simulator comprises:
a first arm comprising a first thermocouple metallic material linked to the power output of the ablator module;
a second arm comprising a second thermocouple metallic material for connection to a monitor display;
a return pathway extending from the first arm to the ablator module, the return pathway permitting passage of RF current and blocking direct current (DC);
an adjustable voltage source producing a direct current (DC) potential and connected via an output circuit across the first arm and the second arm, the output circuit having a greater resistance to RF current than to direct current.

8. The method according to claim 7, wherein the return pathway comprises a DC blocking capacitor.

9. The method according to claim 7, wherein the output circuit comprises a chain of resistors connected in series with an inductor.

10. The method according to claim 9, wherein the inductor comprises a plurality of ferrite inductors in connected in series with the adjustable voltage source.

11. The method according to claim 9, wherein a value of the inductor is 1 mH.

12. A method of testing a thermocouple-based RF ablation system, comprising the steps of:
    connecting a temperature simulator to an ablator module, the ablator module operative to vary a radiofrequency (RF) power output thereof in a predefined manner in response to predefined variations in a temperature signal and having a temperature display monitor;
    delivering RF power from the ablator module to the temperature simulator;
    while performing the step of delivering RF power, performing the steps of:
    communicating temperature signals from the temperature simulator to the ablator module;
    varying a potential of the communicated temperature signals in accordance with known temperature-dependent potentials of a thermocouple junction to represent respective temperatures; and
    calibrating the temperature display monitor to conform to the respective temperatures represented by of the communicated temperature signals.

13. The method according to claim 12, wherein the temperature simulator comprises:
    a first arm comprising a first thermocouple metallic material linked to the power output of the ablator module;
    a second arm comprising a second thermocouple metallic material for connection to a monitor display;
    a return pathway extending from the first arm to the ablator module, the return pathway permitting passage of RF current and blocking direct current (DC);
    an adjustable voltage source producing a DC potential and connected via an output circuit across the first arm and the second arm, the output circuit having a greater resistance to RF current than to direct current.

14. The method according to claim 13, wherein the return pathway comprises a DC blocking capacitor.

15. The method according to claim 13, wherein the output circuit comprises a chain of resistors connected in series with an inductor.

16. The method according to claim 15, wherein the inductor comprises a plurality of ferrite inductors in connected in series with the adjustable voltage source.

17. The method according to claim 15, wherein a value of the inductor is 1 mH.

* * * * *